Dec. 19, 1961 H. M. ZIEGER Plant Pat. 2,111
ROSE PLANT
Filed Nov. 15, 1960
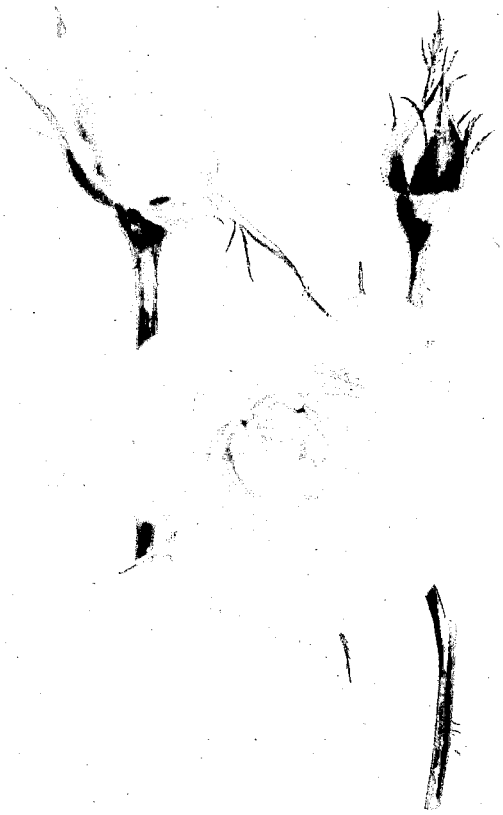
Inventor.
Herman M. Zieger
By: Robb & Robb
Attorneys.

United States Patent Office

Plant Pat. 2,111
Patented Dec. 19, 1961

2,111
ROSE PLANT

Herman M. Zieger, Willow Grove, Pa., assignor, by mesne assignments, to The Conard-Pyle Company, West Grove, Pa., a corporation of Pennsylvania Filed Nov. 15, 1960, Ser. No. 69,531
1 Claim. (Cl. 47—61)

The present invention relates to a new and distinct variety of rose plant of the hybrid polyantha class, which was discovered by me as a cultivated bud sport of the variety named "Rumba" (Plant Patent No. 1,919).

This new variety was discovered by me in my greenhouse at Willow Grove, Pennsylvania, where plants of the variety "Rumba" were being grown under my direction and control. At the time of my discovery aforementioned, my attention was attracted to one particular plant amongst those of the variety "Rumba" by the fact that the plant bore flowers which were substantially different in color from the normal flower color of the variety "Rumba." Ordinarily, flowers of this parent variety are Poppy Red in general color tonality, with the center of each flower Aureolin in color, whereas the flowers of the particular plant that attracted my attention were definitely Orange in color.

Upon closer examination of the plant, I found that it had sported, and I thereupon took steps to preserve the sport, keep in under observation, and later asexually reproduced the same. My continued observation of the original plant and the asexual reproductions thereof, as performed by me by budding at both Willow Grove and London Grove, Pennsylvania, and also performed on my behalf by budding at West Grove, Pennsylvania, fully confirmed the new flower characteristics of the sport and conclusively established that these characteristics come true to form and are transmissible through succeeding propagations.

The accompanying drawing shows typical specimens of the flowers and foliage of my new variety in different stages of development and as depicted in color as nearly true as it is reasonably possible to make the same in a color illustration of this character.

Other than the difference in the color of the flowers of my new sport, as noted in the foregoing, the variety is substantially identical to its parent "Rumba," and accordingly, it is unnecessary to describe the new variety in complete detail, since it conforms to the description appearing in Plant Patent No. 1,919, issued March 1, 1960, to which reference may be readily had. However, for convenience, the following is given as a detailed description of the color and behavior of the flowers of my new variety, with color nomenclature in accordance with the Horticultural Color Chart of the Royal Horticultural Society:

Type: Hardy; bush; greenhouse; outdoor; sport; for cut flowers and for garden decoration.

Class: Hybrid polyantha.

Propagation: Holds its distinguishing characteristics through succeeding propagations by budding.

*Flower*

Locality where grown and observed: West Grove, Pennsylvania.

Bud:

*As calyx breaks.*—Color—Brick Red, Plate 016.

*As first petal opens.*—Color: outside—Brick Red, Plate 016, grading to Jasper Red, Plate 018, over lower half of petal; inside—Mars Orange, Plate 013, becoming tinted with Buttercup Yellow, Plate 5/1, towards base of petal.

This description of a newly opened flower was made from a rose grown in a greenhouse during the month of August at West Grove, Pennsylvania:

*Color.*—Outer petal: outside surface—Delft Rose, Plate 020/1, lightly overlaid with near Rose Opal, Plate 022/1, over upper half of petal, and lightly veined with Mars Orange, Plate 013/2, with point of attachment Aureolin, Plate 4/1; inside surface—near Delft Rose, Plate 020/2, around apical margin, grading to Mars Orange, Plate 013/1, with underlying pigment of Mimosa Yellow, Plate 602/1, becoming more apparent over basal quarter of petal; often point of attachment is surrounded by a halo of near Brick Red, Plate 016. Intermediate petal: outside surface—Mars Orange, Plate 013/1, lightly veined with near Mars Orange, Plate 013/2, and with point of attachment Aureolin, Plate 4/1; inside surface—between Orange, Plate 12/1, and Orange, Plate 12/2, grading to near Lemon Yellow, Plate 4/1, over basal quarter of petal, with two small areas of Brick Red, Plate 016 respectively at opposite sides of point of attachment. Inner petal: outside surface—varying from Mars Orange, Plate 013/1, to Mars Orange, Plate 013, with point of attachment Aureolin, Plate 4/1; inside surface—between Orange, Plate 12/1, and Orange, Plate 12/2, grading to Buttercup Yellow, Plate 5, over basal center part of petal, with two small areas of Brick Red, Plate 016, respectively on opposite sides of point of attachment.

This description was made from a rose that was open for three days in a greenhouse during the month of August at West Grove, Pennsylvania:

*Color.*—Outer petal; outside surface—between Rose Opal, Plate 022/2, and Rose Opal, Plate 022/1, often streaked with Citron Green, Plate 763/3, said latter color carrying on down to the point of attachment; inside surface—Empire Rose, Plate 0621, veined with Citron Green, Plate 763/3, at tip of petal, grading to between Orange, Plate 12/1, and Orange, Plate 12/2, over basal half of petal, with point of attachment Citron Green, Plate 763/3, and having on each side thereof an area of Brick Red, Plate 016/2. Inner petal: outside surface—between Begonia, Plate 619, and Begonia, Plate 619/1, occasionally streaked and veined with Primrose Yellow, Plate 601, with point of attachment also Primrose Yellow, Plate 601; inside surface—Azalea Pink, Plate 618, becoming from Orange, Plate 12/1, to Orange, Plate 12/2, with basal quarter of petal and point of attachment Primrose Yellow, Plate 601.

*General color effect.*—Newly opened flower—between Orange, Plate 12/1, and Orange, Plate 12/2. 3-days open—between Orange, Plate 12/1, and Orange, Plate 12/2, with outer margin of petal Empire Rose, Plate 0621.

*Behavior.*—General color effect—fading to Empire Rose, Plate 0621/1.

*Flower longevity.*—On bush in garden—many days in August. Cut roses grown outdoors and kept at living-room temperatures——many days in August. Cut roses grown in greenhouse and kept at living-room temperatures—at least 10 days or more in August.

I claim:

A new and distinct variety of rose plant of the hybrid polyantha class, substantially as herein shown and described, characterized particularly as to novelty by being generally similar to its parent variety "Rumba" (Plant Patent No. 1,919), but being essentially distinguished therefrom by the Orange general color tonality of its flowers.

No references cited.